United States Patent [19]

Kofod

[11] 4,356,119
[45] Oct. 26, 1982

[54] THERAPEUTICALLY ACTIVE POLYPEPTIDES OR ACID ADDITION SALTS AND A PROCESS FOR PRODUCING SUCH COMPOUNDS

[75] Inventor: Hans Kofod, Lyngby, Denmark

[73] Assignee: Nordisk Insulinlaboratorium, Gentofte, Denmark

[21] Appl. No.: 78,424

[22] Filed: Sep. 24, 1979

[30] Foreign Application Priority Data

Sep. 28, 1978 [DK] Denmark ............................ 4304/78

[51] Int. Cl.³ .................... C07C 103/52; A61K 37/00
[52] U.S. Cl. .............................. 260/112.5 R; 424/177
[58] Field of Search ................. 260/112.5 R; 424/177

[56] References Cited

U.S. PATENT DOCUMENTS

| | | | |
|---|---|---|---|
| 3,400,118 | 9/1968 | Bodanszky et al. | 260/112.5 R |
| 3,474,083 | 10/1969 | Shiga et al. | 260/112.5 R |
| 3,832,337 | 8/1974 | Ondetti et al. | 260/112.5 R |
| 3,842,064 | 10/1974 | Creven | 260/112.5 R |
| 3,850,904 | 11/1974 | Creven | 260/112.5 R |
| 3,853,838 | 12/1974 | Creven | 260/112.5 R |
| 3,856,770 | 12/1979 | Creven | 260/112.5 R |
| 3,975,365 | 8/1976 | Mazur | 260/112.5 R |
| 3,978,035 | 8/1976 | Wunsch et al. | 260/112.5 R |
| 4,024,121 | 5/1977 | Schally et al. | 260/112.5 R |
| 4,058,512 | 11/1977 | Sievertsson | 260/112.5 R |
| 4,075,191 | 2/1978 | Beddell et al. | 260/112.5 R |
| 4,086,220 | 4/1978 | Schlatter | 260/112.5 R |
| 4,107,298 | 8/1978 | Lüning | 260/112.5 R |
| 4,110,321 | 8/1978 | Folkers | 260/112.5 R |
| 4,161,522 | 7/1979 | Hamburger | 260/112.5 R |
| 4,171,299 | 10/1979 | Hamburger | 260/112.5 R |

FOREIGN PATENT DOCUMENTS

| | | | |
|---|---|---|---|
| 616330 | 3/1961 | Canada | 260/112.5 R |
| 685075 | 4/1961 | Canada | 260/112.5 R |
| 798855 | 11/1968 | Canada | 260/112.5 R |

OTHER PUBLICATIONS

V. Mutt, et al., Biochemistry vol. 4, No. 11, Nov. (1965) pp. 2358–2362.

G. Jäger, et al., Chem. Ber. 107, 215–231 (1974).
G. R. Pettit, "Synthetic Peptides" vol. 2, (1973), pp. 66, 67; 76, 77; 128, 129; vol. 1, (1973), pp. 92, 93; 110, 111; 140, 241; 358, 359; 366, 367.

Primary Examiner—Delbert R. Phillips
Attorney, Agent, or Firm—Ladas & Parry

[57] ABSTRACT

Polypeptide derivatives of the formula:

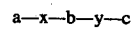

a—x—b—y—c wherein x represents an acidic amino acid, preferably glu or asp, y represents a basic amino acid, preferably arg, lys or his, z represents hydrogen or a small protective group for the α-amino group in x, b represents a bond, a single amino acid or a peptide having up to 10 amino acids in the chain, and c represents —NR¹R², wherein R¹ and R² are selected from the group consisting of hydrogen, $C_1$–$C_6$ alkyl and $C_3$–$C_8$ cycloalkyl, or R¹ and R² together with the attached nitrogen atom form a heterocyclic group optionally containing an additional hetero atom, or c represents —OR³, wherein R³ is selected from the group consisting of $C_1$–$C_6$ alkyl, $C_3$–$C_8$ cycloalkyl, benzyl, phenacyl, phthalimidomethyl, β-methylthioethyl, 4-picolyl or substituted benzyl, or c is a single amino acid, except leu, or an amino acid derivative —z—d with the proviso that —z cannot be leu, and d may be —NR¹R² or OR³, wherein R¹, R², and R³ are as defined above, or acid addition salts of such peptides, may be produced by peptide synthesis methods known per se.

The polypeptides inhibit the glucose stimulated secretion of insulin from Langerhans's islets without affecting the secretion of glucagon, and potentiate the effect of insulin on the metabolism of glucose in isolated fat cells and in vivo potentiate the metabolism of glucose.

2 Claims, No Drawings

THERAPEUTICALLY ACTIVE POLYPEPTIDES OR ACID ADDITION SALTS AND A PROCESS FOR PRODUCING SUCH COMPOUNDS

The present invention relates to a group of new, therapeutically active peptides, a process for producing them, as well as their use. The present peptides are characterized in that in vitro they possess the following properties: they inhibit the glucose stimulated secretion of insulin from Langerhans's islets without affecting secretion of glucagon, and potentiate the effect of insulin on the metabolism of glucose in isolated fat cells, and in vivo potentiate the metabolism of glucose.

The present peptides may be described as follows:

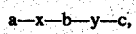

wherein x represents an acidic amino acid, e.g. glutamic acid or aspartic acid, y represents a basic amino acid, e.g. arginine, lysine or histidine, a represents hydrogen or a small protective group for the α-amino group in x, e.g. acetyl or propionyl, etc., b may represent a bond, a single amino acid (e.g. leu, ser, ala, gly, ile, val, thr, lys, arg, asp, asn, glu, gln, met, phe, tyr, trp or his) or peptides having up to 10 amino acids in the chain (e.g. leu-ser, ser-ala, leu-ser-arg-leu, ser-ala-arg-leu-gln or leu-ser-arg-leu-arg-asp-ser-ala), c may represent $-NR^1R^2$, wherein $R^1$ and $R^2$ are selected from the group consisting of hydrogen, $C_1-C_6$ alkyl and $C_3-C_8$ cycloalkyl (e.g. methyl, ethyl, propyl, isopropyl, butyl, tertiary butyl, pentyl, hexyl, cyclopentyl, cyclohexyl, cyclopeptyl, cycloctyl, etc.). $R^1$ and $R^2$ may also be linked together so as to form a cyclic group having at least 1 hetero atom, i.e. the amide bonded nitrogen atom (e.g. pyrrol, pyrroline, pyrrolidine, piperidines, etc.), said group optionally containing an additional hetero atom, such as nitrogen, oxygen, or sulfur (e.g. pyrimidine, morpholine or thiomorpholine), c may also represent $-OR^3$, wherein $R^3$ is selected from the group consisting of hydrogen, $C_1-C_6$ alkyl (methyl, ethyl, propyl, isopropyl, butyl, isobutyl, tertiary butyl, pentyl, hexyl, etc.), $C_3-C_8$ cycloalkyl (cyclopentyl, cyclohexyl, cycloheptyl, cycloctyl, etc.), benzyl, phenacyl, phthalimidomethyl, β-methylthioethyl, 4-picolyl, and substituted benzyl, wherein the substituents are at least one of the following groups: nitro, methoxy, methyl, halogen, (e.g. p-methoxybenzyl, 2,4-di-methoxybenzyl, etc.).

$R^3$ is preferably $C_1-C_6$ alkyl, benzyl or substituted benzyl, or c may represent a single amino acid, except leucine (leu), or an amino acid derivative $-z-d$ with the proviso that $-z$ cannot be leu, but may e.g. by gly, ala, etc., and d may be $-NR^1R^2$ or $OR^3$, wherein $R^1$, $R^2$, and $R^3$ are as defined above.

The invention also relates to acid addition salts of said peptides with acids acceptable to the organism, such as HCl or $CH_3COOH$ and capable of forming salts with the peptides.

The present peptides and peptide derivatives may be produced in a manner known per se, single amino acids or peptides, appropriately protected, being coupled to single amino acids or peptides, likewise appropriately protected, by means of carboxylic acid activating substances, as described in Houben-Weyl: Methoden der organischen Chemie 15/2, Synthesen von Peptiden, p. 2-364 (1), e.g. by means of dicyclohexylcarbodiimide, N-ethyl-N'-(dimethylaminopropyl)-carbodiimide, o-nitrophenol, p-nitrophenol, pentachlorophenol with or without addition of catalyzing substances. Moreover, the peptides may be produced by enzymatic catalysis, e.g. as described by Widmer, F. and Johansen, J. T. (4) or by means of the gene of the individual peptides by the so-called gene manipulation, e.g., as described by Itakura, K. et al. (5).

Trifunctional amino acids forming part of the peptides may either appear unprotected in the side chain group or be protected, $N^G$ which refers to side chain nitrogen in arginine may e.g. be protected with one of the following groups: $H^+$, $-NO_2$, tosyl, t-butyloxycarbonyl or carbobenzoxy. The hydroxy group in serine may e.g. be protected by t-butyl ether or benzyl ether during the synthesis, and the β-acid group in aspartic acid may be protected as benzyl ester. Generally, all the constituent, functional groups may be protected in a manner known per se. Primarily, protective groups are used which may be cleaved hydrogenolytically.

The α-amino groups may be protected by e.g. t-butyloxycarbonyl, carbobenzoxy, adamantyloxycarbonyl or isoborneyloxycarbonyl. Primarily, t-butyloxycarbonyl is used.

A plurality of the present peptides are sequencies or derivatives of sequencies of the intestinal hormone secretin.

Secretin primarily affects the exocrinic pancreas, but is has been demonstrated that secretin in pharmacological dosages potentiate secretion of insulin, without affecting the blood sugar level though, Enk, K. et al. (6). As far as secretin is concerned no effects have been demonstrated which are related to the effects produced by the group of peptides of the invention. The peptide asp-ser-ala-arg-OH is formed in the organism by enzymatic cleavage of the intestinal hormone secretin, but it is mentioned in the literature (2) that the whole secretin molecule must be present to produce biological activity. However, it is described in the U.S. Pat. No. 4,086,220 that the secretin fragments 1-15, 1-16, 1-17, and 1-18 like secretin possess biological activity on the exocrinic pancreas.

It has now surprisingly been found that the present peptides, which structurally are derived from secretin, have an effect which is totally different from secretin, and that this effect may be used for treating newly discovered, juvenile diabetics whose Langerhan's islets it is desired to protect. The peptides prevent the islets from giving off insulin, and at the same time the necessary amount of insulin to be administered to maintain normal conditions is diminished.

In vitro determination of the insulin potentiating effect of the peptides on the metabolism of glucose has given the following results, the general methods being described elsewhere (3).

TABLE I

|   |   |   | 100 μg/ml | 10 μg/ml | 1 μg/ml | 0.1 μg/ml | 0.01 μg/ml | 0 μg/ml | Peptide |
|---|---|---|---|---|---|---|---|---|---|
| 1 | 0 | ng/ml | 22 | 22 | 22 | 22 | 22 | 22 | |
|   | 0.6 | ng/ml | 108 | 91 | 88 | 90 | 94 | 79 | |
|   | 50 | ng/ml | 126 | 113 | 112 | 113 | 118 | 100 | |
| 2 | 0 | ng/ml | 15 | 20 | 21 | 20 | 20 | 22 | |
|   | 0.6 | ng/ml | 55 | 85 | 86 | 88 | 83 | 81 | |
|   | 50 | ng/ml | 70 | 112 | 108 | 112 | 114 | 100 | |

TABLE I-continued

| | | | 100 μg/ml | 10 μg/ml | 1 μg/ml | 0.1 μg/ml | 0.01 μg/ml | 0 μg/ml | Peptide |
|---|---|---|---|---|---|---|---|---|---|
| 3 | 0 | ng/ml | 16 | 8 | 8 | 8 | 8 | 8 | |
| | 0.6 | ng/ml | 100 | 80 | 80 | 85 | 90 | 78 | |
| | 50 | ng/ml | 124 | 108 | 108 | 112 | 114 | 100 | |
| 6 | 0 | ng/ml | 10 | — | — | — | — | 10 | |
| | 0.6 | ng/ml | 89 | — | — | — | — | 62 | |
| | 50 | ng/ml | 121 | — | — | — | — | 100 | |
| | Insulin | | | | | | | | |

1 glu-leu-ser-arg-OMe, 2HCl
2 glu-leu-ser-arg-leu-arg-OMe, 3HCl
3 asp-ser-ala-arg-OMe, 2HCl
6 glu-gly-gly-gly-arg-OMe, 2HCl The table shows the glucose metabolism in fat cells as a function of present insulin and peptide, 50 ng/ml of insulin+0 μg/ml of peptide being put equal to 100%. All other values are based on this.

In vitro determination of the effect of the peptides on the glucose stimulated insulin secretion was carried out on Langerhan's islets isolated by collagenase technique and preincubated 24 hours at 37° C. Secretion tests were conducted with 10 mM of glucose and three peptide concentrations.

| peptide | 5 × 10⁻² mmolar | 5 × 10⁻ mmolar | 5 mmolar |
|---|---|---|---|
| 1 | 76 | 59 | 51 |
| 2 | 66 | 73 | 113 |
| 3 | 72 | 55 | 63 |
| 4 | 96 | 41 | 9 |
| 5 | 65 | 43 | 10 |
| 6 | 66 | 46 | 41 |

1 glu-leu-ser-arg-OMe, 2HCl
2 glu-leu-ser-arg-leu-arg-OMe, 3HCl
3 asp-ser-ala-arg-OMe, 2HCl
4 glu-leu-ser-arg-leu-arg-asp-ser-ala-arg-OMe, 4HCl
5 asp-ser-ala-arg-leu-arg-gln-arg-OMe, 3HCl
6 glu-gly-gly-gly-arg-OMe, 2HCl All peptides have been tested in the form of their hydrochlorides together with 10 mM of glucose, and the values are calculated as a percentage of the effect of 10 mM of glucose alone.

The peptides may be administered as injection preparations admixed with insulin or without the presence of insulin. They may also be administered per os.

EXAMPLES

All the amino acids mentioned in the specification are the naturally occurring L-forms and their abbreviations follow the 3-letter abbreviations laid down by IUPAC-IUB.

Further, the following abbreviations are used.

| BOC: | t.butyloxy-carbonyl | TLC: | thin layer chromatography |
|---|---|---|---|
| DMF: | dimethyl-formamide | AcOH: | acetic acid |
| TEA: | triethylamine | MeOH: | methanol |
| ONO: | o-nitrophenyl | BAW623: | butanol-1:acetic acid:water = 6:2:3 |
| ONP: | p-nitrophenyl | | |
| | | BAWP: | butanol 1:acetic acid:water:pyridine = 30:6:24:20 |
| EE: | ethylacetate | | |
| Bzl: | benzly | HBT: | hydroxybenzotriazole |
| TFA: | trifluoroacetic acid | SHI: | chloroform-methanol-acetic acid = 90:5:5 |
| PCP: | pentachloro-phenyl | | |
| AAA: | amino acid | DAPECI: | dimethylaminopropyl- |
| analysis | | | ethyl-carbodiimide |

Analyses of amino acids were carried out on Beckman 120C Amino-acid Analyzer.

TLC was carried out in BAW (A) and BAWP (B) and SHI (c).

The purity criterion for protected peptides is the presence of only one spot in TLC in liquid A and C.

The following examples are representative of the reactions used.

EXAMPLE 1 asp-ser-ala-arg-OMe, 2HCl

BOC-ala-(NO₂)arg-OMe 5 g of (NO₂)arg-OMe, HCl were suspended in 75 ml of DMF. 2,500 μl of TEA and 5 g of BOC-ala-ONO were added. After 20 hours' reaction the BOC-ala-ONO was used up, and the reaction was evaporated to a yellow oil which was dissolved in 150 ml of EE. The EE-phase was thoroughly washed with saturated NaHCO₃ to remove the produced O-nitrophenol. Then the product was evaporated again and the residue was dissolved in 25 ml of EE to which dry ether was added until constant cloudiness. Standing for three days at 5° C. for precipitation. The product was isolated, washed with dry ether and dried at a reduced pressure. Yield: 4 g=66% of the theoretical one.

BOC—(OBzl)ser-ala-arg-OMe 4 g of BOC-ala-(NO₂)arg-OMe were dissolved in TFA (50 ml) and left to stand with stirring for 20 minutes. Dry ether (150 ml) was added. Left to stand for 30 minutes with stirring to precipitate salt. The peptide TFA salt was isolated by centrifugation and washed with dry ether. The dried salt was dissolved in 35 ml of DMF and there was added 2 ml of TEA and 4,2 g of BOC-(OBzl)-ser-ONO. After 24 hours the reaction was finished, evaluated by TLC. DMF was evaporated at a reduced pressure at 30°-35° C. EE (150 ml) was added, and the product was washed with 5% NaHCO₃ and H₂O.

The EE-phase was evaporated to a small volume to which petroleum ether 60°-80° was added until constant cloudiness. The mixture was left to stand in the cold until negative test for product in supernatant. The product was isolated and washed with dry ether and dried at a reduced pressure. Yield: 5 g=87% of the theoretical one.

BOC-(β-Bzl)asp-(OBzl)ser-ala-(NO₂)arg-OMe 3 g of BOC-(OBzl)ser-ala-(NO₂)arg-OMe were dissolved in 25 ml of TFA. Left to stand for 20 minutes with stirring. 150 ml of ether were added to precipitate the peptide TFA salt which was isolated by centrifugation and repeated washing with dry ether. The peptide TFA salt was dissolved in 25 ml of DMF to which 2.5 g of BOC-(β-Bzl)asp-ONO and 800 μl of TEA in 100 μl portions were added over 8 hours. After 20 hours the reaction was finished, and DMF was evaporated at a reduced pressure at 30°-35° C. EE was added, precipitating the product. Standing in the cold until negative test for peptide in the supernatant. The product was isolated and thoroughly washed with dry ether. Yield: 3.6 g=88% of the theoretical one.

asp-ser-ala-arg-OMe, 2HCl 3.6 g of BOC-(β-Bzl)asp-(OBzl)ser-ala-(NO₂)arg-OMe were hydrogenated with 3 g of Pd/C 10% in 10% AcOH/MeOH until the theoretical amount of hydrogen was taken up and until TLC showed a substance in addition to produced ammonium acetate. The peptide was isolated by filtration, thorough washing of catalyst and evaporation to an oil. Produced ammonium acetate was removed by a single run on a dry silica gel column with 5% AcOH/MeOH. The isolated, pure, BOC-protected peptide was treated with 1 N HCl/AcOH for 30 minutes. The substance was isolated by precipitation with dry ether and thorough washing of the precipitate with dry ether. Yield: 2 g=82% of the theoretical one.

Amino acid analysis gave the following result:
asp:ser:ala:arg=1.01:0.69:1.00:0.92.
Serine is low owing to the method of hydrolysis.
Rf$_{(A)}$=0.08 Rf$_{(B)}$=0.25
M.p. (decomp.) 164
Total yield: 44% of the theoretical one.

EXAMPLE 2 asp-ser-ala-arg-leu-gln-arg-OMe, 3HCl was produced by the procedure of example 1.

EXAMPLE 3 glu-leu-ser-arg-leu-arg-asp-ser-ala-arg-OMe, 4HCl

BOC-(NO₂)arg-(βBzl)asp-(OBzl)ser-ala-(NO₂)arg-OMe 1.5 g of BOC-(βBzl)asp-(OBzl)ser-ala-(NO₂)arg-OMe were treated with 30 ml of TFA for 20 minutes. 200 ml of dry ether were added to precipitate the TFA salt. The salt was isolated and thoroughly washed with dry ether and was then dried at a reduced pressure. The peptide TFA salt was dissolved in 30 ml of DMF, to which 1.4 g of BOC-(NO₂)arg-PCP, 1.4 g of HBT and 225 μl of diisopropylethylamine were added.

The reaction mixture was evaporated to a yellow oil which was dissolved in 200 ml of EE. The EE-phase was thoroughly washed with NaHCO₃ (5%, 3×50 ml) and water (3×50 ml). The EE-phase was dried with MgSO₄, filtered and evaporated to an amorphous substance which was washed with EE. Yield: 1.35 g=72%.

BOC-leu-(NO₂)arg-(βBzl)asp-(OBzl)ser-ala-(NO₂)arg-OMe 950 mg of BOC-(NO₂)arg-(β-Bzl)asp-(OBzl)ser-ala-(NO₂)arg-OMe were treated for 15 minutes with 20 ml of TFA. 200 ml of dry ether were added to precipitate the product. The product was isolated and thoroughly washed with dry ether. The peptide TFA salt was dried at a reduced pressure.

The salt was dissolved in 20 ml of DMF to which were added 700 mg of BOC-leu-ONO and 150 μl of TEA. After 11 hours' reaction the peptide salt was used up, and the reaction mixture was evaporated to a yellow oil. Addition of 50 ml of EE precipitates the desired 6-peptide. Thorough washing with EE resulted in a pure product. Yield: 1.0 g=94%.

BOC-(NO₂)arg-leu-(NO₂)arg-(βBzl)asp-(OBzl)ser-ala-(NO₂)arg-OMe 1 g of BOC-leu-(NO₂)arg-(βBzl)asp-(OBzl)ser-ala-(NO₂)arg-OMe was treated for 15 minutes with 15 ml of TFA. Then there were added 200 ml of dry ether to precipitate the peptide TFA salt. The salt was isolated and thoroughly washed with dry ether and dried at a reduced pressure. The peptide salt was dissolved in 20 ml of DMF to which there were added 1.7 g of BOC-(NO₂)-arg-PCP, 400 mg of HBT and 130 μl of TEA.

After finished reaction the product was evaporated at a reduced pressure to a brownish oil which solidified when EE was poured over it. The precipitate was thoroughly washed with EE (4×100 ml) and water (3×100 ml). The product was dried at a reduced pressure. Yield: 1.1 g=93%.

BOC-(OBzl)ser-(NO₂)arg-leu-(NO₂)arg-(βBzl)asp-(OBzl)ser-ala-(NO₂)-arg-OMe 800 mg of BOC-(NO₂)arg-leu-(NO₂)arg-(βBzl)asp-(OBzl)ser-ala-(NO₂)-arg-OMe was treated for 15 minutes with 15 ml of TFA. 150 ml of dry ether were added to precipitate the peptide TFA salt. The salt was isolated, thoroughly washed with dry ether and dried at a reduced pressure. The salt was dissolved in 20 ml of DMF to which 1 g of BOC-(OBzl)ser-ONO and 90 μl of TEA were added.

After 5 days the reaction was over, and the product was evaporated to a yellowish oil to which 75 ml of EE were added to precipitate the protected 8-peptide. The peptide was isolated and thoroughly washed with EE. Yield: 800 mg=88%.

BOC-leu-(OBzl)ser-(NO₂)arg-leu-(NO₂)arg-(βBzl)asp-(OBzl)ser-ala-(NO₂)arg-OMe 600 mg of BOC-(OBzl)ser-(NO₂)arg-leu-(NO₂)arg-(βBzl)asp-(OBzl)-ser-ala-(NO₂)arg-OME were treated with 15 ml of TFA for 15 minutes, and then the peptide TFA salt was precipitated with 150 ml of dry ether. The peptide TFA salt was washed thoroughly with dry ether and dried at a reduced pressure.

The peptide TFA salt was dissolved in 25 ml of DMF to which 55 μl of TFA and 1.3 g of BOC-leu-ONO were added.

After the termination of the reaction the product was evaporated to a crystalline substance to which EE was added to precipitate protected 9-peptide. The protected peptide was thoroughly washed with EE. The product was dried at a reduced pressure. Yield: 550 mg=85%.

BOC-(αBzl)glu-leu-(OBzl)ser-(NO₂)arg-leu-(NO₂)arg-(βBzl)asp-(OBzl)ser-ala-(NO₂)arg-OMe 350 ml of BOC-leu-(OBzl)ser-(NO₂)arg-leu-(NO₂.)arg-(βBzl)asp-(OBzl)ser-ala-(NO₂)arg-OMe were treated for 15 minutes with 15 ml of TFA. 200 ml of dry ether were added to precipitate the peptide TFA salt. The salt was isolated, thoroughly washed with dry ether and dried at a reduced pressure.

The peptide TFA salt was dissolved in 15 ml of DMF to which were added 75 μl of TEA and 1.2 g of BOC-(α-Bzl)glu-ONO.

After terminated reaction DMF was evaporated at a reduced pressure, and 50 ml of EE were added to precipitate the product. The protected 10-peptide was isolated and thoroughly washed with EE until negative reaction for O-nitrophenol and BOC-(α-Bzl)glu-ONO. Yield: 350 mg=88%.

glu-leu-ser-arg-leu-arg-asp-ser-ala-arg-OMe, 4HCl 350 mg of protected 10-peptide were hydrogenated with 600 mg of 10% Pd/C in a mixture of 25 ml of methanol, 25 ml of DMF and 10 ml of AcOH. After finished reaction the catalyst was filtered off and thoroughly washed. The collected extracts were evaporated to an oil which was purified by preparative TLC. The isolated, pure amino-terminal-protected 10-peptide was treated with 25 ml of 1 N HCl/AcOH for 30 minutes, and then the desired product was precipitated by the addition of dry ether. The product was thoroughly washed with dry ether and dried at a reduced pressure. Yield: 200 mg=71% of the theoretical one.

Determination of amino acid:
Theory: glu:leu:ser:ala:asp:arg=1:2:2:1:1:3
Practice: 1.06:1.90:1.55:1.00:1.09:3.1
M.p.: 170° C. (decomp.)
TLC: $R_{(A)}$=0.08 $R_{(B)}$=0.29

EXAMPLE 4

The product glu-leu-ser-arg-leu-arg-OMe, 3HCl was produced by the procedure of example 3.

EXAMPLE 5 glu-leu-ser-arg-OMe, 2HCl

BOC-(OBzl)ser-($NO_2$)arg-OMe 6 g of BOC-(OBzl)ser were dissolved in 50 ml of $CH_2Cl_2$ and cooled to −5° C. 4 g of DAPECI in 100 ml of $CH_2Cl_2$ were added slowly and dropwise. This was admixed with a mixture of 5 g of ($NO_2$)arg-OMe, HCl and 2.8 ml of TEA in 100 ml of DMF. After the termination of the reaction the product was evaporated at a reduced pressure. 50 ml of water and 150 ml of EE were added. The organic phase was washed with water, 5% $NaHCO_3$, water, 10% citric acid and water. The EE-phase was dried with $Na_2CO_4$.

After filtration and evaporation to an oil the product was obtained by pouring petroleum ether over it, and was isolated as an amorphous, white substance. Yield: 7 g=75%.

BOC-(α-Bzl)glu-leu-ONP 1.4 g of BOC-(α-Bzl)glu was dissolved in 50 ml of $CH_2Cl_2$ and cooled to −5° C. 1 g of DAPECI in 25 ml of $CH_2Cl_2$ was slowly added thereto so that the temperature did not exceed −2° C. After 30 minutes was added 1 g of leu-ONP, HCl in crystalline form, and 485 μl of TEA in 25 ml of $CH_2Cl_2$ were added dropwise over a period of 6 hours.

After finished reaction the product was evaporated at a reduced pressure. The mixture was taken up in EE, which was subjected to one, rapid extraction with 0.1 N NaOH and three extractions with water. The EE-phase was then dried.

Evaporation of the EE-phase crystallized the product. Yield: 1.2 g=66%.

BOC-(αBzl)glu-leu-(OBzl)ser-($NO_2$)arg-OMe 1.5 g of BOC-(OBzl)ser-($NO_2$)arg-OMe were treated with 20 ml of 1 N HCl/AcOH for 15 minutes. 150 ml of dry ether were added for precipitation. The precipitate was isolated, thoroughly washed with dry ether and dried.

1.2 g of BOC-(αBzl)glu-leu-ONP were dissolved in 50 ml of DMF to which were added (OBzl)ser-($NO_2$)arg-OMe, HCl and TEA until basic reaction.

The reaction was kept slightly basic for 6 days, and then the mixture was evaporated at a reduced pressure. EE was added, precipitating unreacted (OBzl)ser-($NO_2$)arg-OMe.

The EE-phase was thoroughly extracted with 3×30 ml of 10% citric acid, water, 2×50 ml of 0.1 N NaOH and water.

The EE-phase was dried, filtered and evaporated to a white, amorphous substance which was pure after TLC. Yield: 1.31 g=77%.

glu-leu-ser-arg-OMe, 2HCl 1.31 g of BOC-(αBzl)glu-leu-(OBzl)ser-($NO_2$)arg-OMe were hydrogenated over 1 g of Pd/C (10%) in 150 ml of 10% AcOH/MeOH.

After finished reaction the catalyst was filtered off and thoroughly washed. The collected organic phases were evaporated at a reduced pressure to an oil.

The oil was dissolved in 20% AcOH and freeze dried.

The freeze dried substance was dissolved in 50 ml of 1 N HCl/AcOH and left to stand for 30 minutes. 200 ml of dry ether were added for precipitation. The precipitated product was thoroughly washed with dry ether and dried. Yield: 600 mg=66%.

M.p. (decomp.)=160° C.
Amino acid analysis: glu:leu:ser:arg=1:1:1:1
Practice: 1.07:1.00:0.71:0.84
TLC: $R_{(A)}$=0.21 $R_{(B)}$=0.47

EXAMPLE 6

An injectable preparation may e.g. be produced in the following manner: 3.08 mg of asp-ser-ala-arg-OMe, 2HCl are dissolved in 200 μl of 0.9% NaCl. This solution is added to 20 ml of insulin solution (40 IU/ml), resulting in a solution which is equimolar in peptide and insulin. The proportion between peptide and insulin may, if desired, be changed to produce different degrees of efficiency.

BIBLIOGRAPHY

1. Houben-Weyl: Methoden der organischen Chemie 15/2, Synthesen von Peptiden, p. 2–364, (1974), Georg Thieme Verlag, Stuttgart.
2. J. E. Jorpes and V. Mutt. Secretin, Cholecystokinin, Pancreozymin and Gastrin, p. 30 (1973), Springer-Verlag, Berlin.
3. Gliemann, J., Diabetologia 3, 382 (1967).
4. Widmer, F. and Johansen, J. T., Carlsberg. Res. Commun., vol. 44, p. 3746 (1979).
5. Itakura, K. et al., Science 198, p. 1056 (1977).
6. Enk, B., Kolendorf, K., Deckert, T.—Ugeskrift for Laeger (weekly publication for doctors), 134, No. 49, p. 2577–80 (1972).

I claim:
1. A polypeptide derivative of the general formula:

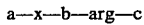

wherein x represents glu or asp,
a represents hydrogen or a small protective group for the α-amino group in x,
b represents leu, a di- or tripeptide selected from the group consisting of leu-ser, ser-ala, his-phe, and gly-gly-gly, or when x is glu, b may also represent a bond or a secretin fragment selected from the group consisting of leu-ser-arg-leu and leu-ser-arg-leu-arg-asp-ser-ala, or when x is asp, b may also represent the secretin fragment ser-ala-arg-leu-gln,
c represents —$NR^1R^2$, wherein $R^1$ and $R^2$ are selected from the group consisting of hydrogen and $C_1$–$C_6$ alkyl or c represents —$OR^3$, wherein $R^3$ is selected from the group consisting of hydrogen and $C_1$–$C_6$ alkyl, except that when x is asp and b is ser-ala $R^3$ is not hydrogen, or acid addition salts of such peptides with acids acceptable to the organism.

2. A polypeptide derivative of the general formula of claim 1, wherein a is hydrogen or an acyl group and b is selected from the group consisting of leu, leu-ser, ser-ala, leu-ser-arg-leu, ser-ala-arg-leu-gln and leu-ser-arg-leu-arg-asp-ser-ala.

* * * * *